United States Patent
Kendig et al.

(10) Patent No.: US 9,266,733 B2
(45) Date of Patent: *Feb. 23, 2016

(54) MULTILAYER SELF-DECONTAMINATING COATINGS (75) Inventors: Martin W. Kendig, Thousand Oaks, CA (US); Young J. Chung, Calabasas, CA (US); Alan B. Harker, Thousand Oaks, CA (US); Dennis R. Strauss, Ventura, CA (US)

(73) Assignee: TELEDYNE SCIENTIFIC & IMAGING, LLC, Thousand Oaks, CA (US)

( * ) Notice: Subject to any disclaimer, the term of this patent is extended or adjusted under 35 U.S.C. 154(b) by 2203 days.

This patent is subject to a terminal disclaimer.

(21) Appl. No.: 11/241,518

(22) Filed: Sep. 30, 2005

(65) Prior Publication Data
US 2007/0278109 A1    Dec. 6, 2007

(51) Int. Cl.
C23C 8/02 (2006.01)
C01B 7/14 (2006.01)
A61L 2/232 (2006.01)
C23C 26/00 (2006.01)
C23C 30/00 (2006.01)

(52) U.S. Cl.
CPC . C01B 7/14 (2013.01); A61L 2/232 (2013.01); C23C 8/02 (2013.01); C23C 26/00 (2013.01); C23C 30/00 (2013.01)

(58) Field of Classification Search
USPC ............................... 204/242–275.1
See application file for complete search history.

(56) References Cited

U.S. PATENT DOCUMENTS

| | | | |
|---|---|---|---|
| 4,583,548 A | 4/1986 | Schmid | 128/639 |
| 4,798,870 A | 1/1989 | Lyle, Jr. et al. | |
| 5,154,920 A | 10/1992 | Flesher et al. | |
| 5,236,703 A | 8/1993 | Usala | |
| 5,250,160 A | 10/1993 | Oksman et al. | 204/131 |
| 5,252,291 A | 10/1993 | Tsao | 422/23 |
| 5,290,483 A * | 3/1994 | Kulkarni et al. | 252/500 |

(Continued)

FOREIGN PATENT DOCUMENTS

| | | |
|---|---|---|
| JP | 60249265 A | 12/1985 |
| WO | WO0128598 A | 4/2001 |

(Continued)

OTHER PUBLICATIONS

Zelazowska, Elzbieta et al., "Sol-gel derived Li-ion conducting polymer electrolytes", *Materials Science-Poland*, vol. 23, No. 1, p. 177-194 (2005).

(Continued)

*Primary Examiner* — Arun S Phasge
(74) *Attorney, Agent, or Firm* — Koppel, Patrick, Heybl & Philpott (57) ABSTRACT

A layered construction for application to a device or substrate or placement in an enclosed space for use in decontaminating the underlying surface or enclosed space comprises a cathode, an electrolyte layer, an anode and a protective surface layer. A compound that can be electrically decomposed to release on demand and over an extended period of time, an oxidant is included in the layered structure, preferably in the electrolyte layer. Preferred compounds are those which can release halogen ions which react with various different chemical or biological contaminants which may contact the protective layer, destroying, or devitalizing the contaminants.

21 Claims, 6 Drawing Sheets

(56) References Cited

U.S. PATENT DOCUMENTS

| | | | |
|---|---|---|---|
| 5,344,531 A * | 9/1994 | Saito et al. | 205/701 |
| 5,431,908 A | 7/1995 | Lund | 424/78.1 |
| 5,639,452 A | 6/1997 | Messier | |
| 5,665,492 A | 9/1997 | Sotomura | |
| 6,057,488 A | 5/2000 | Koper et al. | 588/200 |
| 6,315,886 B1 * | 11/2001 | Zappi et al. | 205/701 |
| 6,482,309 B1 * | 11/2002 | Green et al. | 205/619 |
| 6,555,055 B1 | 4/2003 | Cisar et al. | 422/28 |
| 6,562,885 B1 | 5/2003 | Moorehead et al. | |
| 6,566,574 B1 | 5/2003 | Tadros et al. | |
| 7,033,509 B2 | 4/2006 | Klein et al. | 210/753 |
| 7,172,734 B1 * | 2/2007 | Joshi | 422/186 |
| 2004/0045479 A1 | 3/2004 | Koper et al. | |
| 2004/0109853 A1 | 6/2004 | McDaniel | |

FOREIGN PATENT DOCUMENTS

| | | |
|---|---|---|
| WO | WO0200267 A | 1/2002 |
| WO | WO2008018856 A | 2/2008 |

OTHER PUBLICATIONS

U.S Appl. No. 2003/0009127 A1; Jan. 9, 2003; Trescony et al.

A. Alimova, A. Katz, P. Gottlieb, and R. R. Alfano, "Proteins and Dipicolinic Acid Released During Heat Shock Activation of Bacillus Subtilis Spores Probed by Optical Spectroscopy"; Applied Optics, 45:445-450; 2006.

PCT Notification of the International Search Report and the Written Opinion of the International Searching Authority, Dated Jul. 7, 2008; for International Application No. PCT/US2006/027751.

* cited by examiner

MULTILAYER SELF-DECONTAMINATING COATINGS

This invention was made with Government support under HR0011-04-C-0130 awarded by the Defense Advanced Research Projects Agency (DARPA). The Government has certain rights in this invention.

The present invention relates primarily to a multi-layered electrically activated coating or appliqué applied to devices or substrates, particularly electronic and circuit components which can be automatically activated or activated at the option of the user to release an oxidizing agent to decontaminate the surface of the substrate or device while not being destructive of the underlying substrate or the surrounding environment. The invention also provides a multi-layered electrolytic cell which can release controlled amounts of a decontaminating agent into an enclosed space. In particular, the oxidizing agent is effective in deactivating or substantially reducing the effectiveness of certain chemically and biologically active agents that it comes in contact with. The coating or cell can also be readily reactivated after activation and depletion.

BACKGROUND

The surfaces of devices, and particularly electronics enclosed within or behind a protecting structure, such as a control panel, or a enclosing case, are particularly difficult to decontaminate once exposed to contaminating or toxic chemical or biological agents. The difficulties result in part from the inability to gaining access to the enclosed space and, after access is accomplished, introducing any decontaminating agents into small spaces in or behind the devices or components thereof. Still further, many decontaminating agents are delivered as aqueous solutions. The aqueous solvent can also be detrimental to the functionality of the device being decontaminated, causing the electrical components to short circuit and metal components to oxidize (rust).

There are numerous examples of decontamination agents that can be applied to a contaminated surface after the surface has been exposed to a contaminant. For example, U.S. Pat. No. 6,566,574 covers a composition including a solubilizing agent for the contaminant, particularly cationic surfactants, and at least one reactive compound that attacks or neutralizes the contaminant. Published US Application 2004/0045479, and its parent U.S. Pat. No. 6,057,488, discloses the use of finely divided metal oxides of hydroxides, which are applied to contaminated surfaces. There are also examples of coatings of various different compositions. For example, Published US Applications 2004/01109853 and 2004/0109853 disclose a coating containing a phosphoric acid triestester hydrolase. U.S. Pat. No. 6,566,574 to Tadros et al discloses materials delivered as foams, sprays, liquids, fogs or aerosols to neutralize chemical or biological agents already contaminating a surface.

U.S. Pat. No. 6,562,885 to Moorehead et al is directed to a substance capable of devitalizing hazardous biological agents and deactivating hazardous chemical agents comprising an activated anion exchange resin having a particle size in the range of about 0.1-300 microns, the resin particles being iodinated by exposure to a sufficient amount of an iodine-substance absorbable by the anion exchange. The resin particles absorb the iodine-substance converting the resin particles into activated resin particles. The iodine-substance is selected from the group consisting of $I_2$ (i.e., diatomic iodine), and polyiodide ions having a valence of −1. The activated resin particles are placed into contact with the biological or chemical agent after contamination as a dry aerosol, by dust coating, or by admixing the particles with a carrier to form a coating. The activated resin particles can also be applied to the surface of an object, providing a continuously active coating (active once applied; can not be activated at will or when the contamination is present).

U.S. Pat. No. 5,639,452 to Messier discloses a disinfectant substance comprising an iodine impregnated ion exchange resin which is a demand-type broad spectrum resin-polyiodide disinfectant useful in sterilizing fluids, and particularly a polyiodide that leaves behind nondetectable or otherwise acceptable residual diatomic iodine in treated fluids. U.S. Pat. No. 5,431,908 to Lund also teaches a method of preparing halide-impregnated ion exchange resins useful in purifying fluids such as water.

U.S. Pat. No. 5,236,703 is directed to a polymeric substrate, such as rubber or latex, that incorporates povidone-iodine which acts as a controlled release biologically active agent.

U.S. Pat. No. 5,154,920 discloses a liquid disinfectant composition which can be used to coat surfaces of a substrate with a polymeric film to impart prolonged germicidal properties to the coated surface by inclusion of phenols, or quaternary ammonium salts.

U.S. Pat. No. 4,798,870 is directed to hydrohalide-polyhalides or quaternary halide-perhalide salts which are bound to polymeric surfaces, such as a fabric or polymer film, using a vinylpyridine as a binding agent.

SUMMARY

The present invention comprises a layered construction for application to a device or substrate. The layered structure comprises as films, a cathode, an electrolyte layer, an anode and a protective surface layer. A compound that can be electrically decomposed to release, on demand and over an extended period of time, an oxidant is included in the layered structure, preferably in the electrolyte layer. Preferred compounds are those which can release halogen ions which react with various different chemical or biological contaminants which may contact the protective layer, destroying, or devitalizing the contaminants.

DETAILED DESCRIPTION

The invention relates to a devitalizing agent or disinfectant containing structure that can be applied as a coating to objects, or provided as free standing delivery means which is inert once applied to the object and which can be automatically or manually activated once a contaminating chemical or biological agent is detected. The invention also includes structure necessary for activating the coating or delivery means and may further include sensors to detect contamination of the surface and, in turn, cause the decontaminating ingredients to be released. Such a substance and structure can be used, for example, to decontaminate solid surfaces, substrates, or mechanical and electronic devices that are exposed to biological agents, such as airborne pathogens and chemical agents, whether exposure is continuous or intermittent. The coating could also be used to provide a protective barrier on such surfaces and devices that are likely be exposed to biological and chemical agents so that they can be devitalized on demand, at least until the active agent present in the coating has been exhausted, without significant detriment to the device's usual utility and without requiring the external supply of decontamination substances or using decontaminating procedures after exposure to the agent. Such a protective coating is also useful on objects that are likely to be exposed to contaminating agents on a more or less regular basis, for example, equipment used in medical emergency response or other health care applications or surfaces in public facilities. The coating and activating structure is also useful on objects that may be exposed to such agents in the event of a catastrophe, such as a military conflict, terrorist incident or a hazardous material spill.

As used herein, "biological agent" refers to hazardous biological organisms including viruses and bacteria, whether in the form of spores or otherwise, parasites, and biologically generated toxins such as botulinum toxin. The term "devitalize" means to kill a biological agent that is an organism, or to render a biological agent inactive or substantially less effective, including, without limitation, disinfection. It is expected that the devitalizing substance will be effective against biological agents that are susceptible to oxidation by ionic halides such as polyiodide ions.

It also would be desirable to have a deactivating substance capable of reaction with and at least partially deactivating certain chemical agents. As used herein, "chemical agent" means a chemical compound, including but not limited to chemical warfare agents such as the compounds known as GD, HD and VX, as well as industrial chemical compounds which may be hazardous. The term "deactivate" also refers to the ability to render any chemical agent inactive, ineffective, or substantially less effective for its intended purpose, and particularly agents hazardous to human, life or health. As described above in connection with devitalization of biological agents, the coatings as described herein are effective against chemical warfare agents and other chemical agents susceptible to oxidation by ionic halides such as polyiodide ions.

Compositions incorporating the features described herein can be applied to substrates to form a protective coating thereon. They can be admixed with a suitable carrier and the resultant coating applied to a substrate by any suitable means, for example, brushing, rolling, spraying, pouring or the like. The carrier may be a paint-type coating such as a water- or organic solvent-based or a polymeric material. Alternatively the composition can be applied on top of an adhesive previously coated on a non-stick carrier, such as a polymer film. The composition with adhesive (an adhesive backed appliqué) can then be removed from the carrier and applied to desired surface, with the adhesive contacting that surface.

These and other objects of the present invention will be apparent from the specification that follows and the appended claims.

Figure 1:
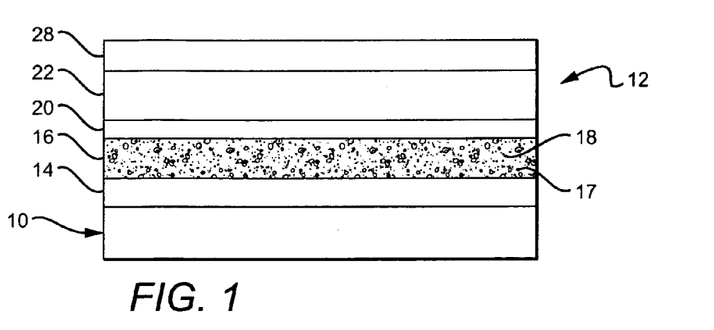
FIG. 1 is a schematic drawing of a device, structure or substrate including a coating comprising a multilayered electrochemical cell incorporating features of the invention.

Referring to FIG. 1, in a particular embodiment, a device, structure or substrate 10 includes a coating comprising a multilayered electrochemical cell 12 incorporating features of the invention comprising, 1) a depolarizable cathode 14 comprising a first conductive coating layer applied to the device, structure or substrate 10,
2) a second layer (the electrolyte layer) 16 on the cathode 14 containing a compound 18 in a surrounding matrix 17, the compound 18 producing a decontaminating oxidant under suitable conditions of polarization,
3) a porous, conductive anode 20, and
4) a porous surface layer 22 which may be hydrophobic, or optionally include a hydrophobic, superhydrophobic or partially hydrophobic surface coating 28. An example of a partially hydrophobic surface is a patterned surface with non-hydrophobic pattern portions.

The electrolyte layer 16 preferably comprises a non-hydroscopic solid, semi-solid (gel) or matrix which includes a liquid entrapped therein, the layer being ionically conducting but electrically non-conducting. The ionic characteristics are provided by chemical compounds which can release an ionizing reagent, such as a halide salt that can release halogen ions ($I^-$, $Cl^-$, $Fl^-$ or $Br^-$) once activated. However, at the same time the matrix of the electrolyte layer 16 should be electrically nonconducting, (electrically insulating), hydrophobic, and chemically stable in the presence of the generated oxidant. Polyethylene oxide, Nafion (a perfluorinated polymer) and crystalline $RbAg_4I_5$ are examples of suitable solid electrolytes. However, one skilled in the art will recognize that other solid electrolytes can be used. Examples of a suitable ionic semi-liquid gels include but are not limited to materials used in dye sensitive solar cells and electrochromic glass, quaternary alkyl ammonium in alkyl carbonate/polyacrylonitrile (PAN) gels with organic solvents and solgels derived from porous silica gels such as Ormolyte, formed from tetraethyl orthosilicate (TEOS) and polyethylene glycol (PEG), which are each doped with an ionic liquid containing the halide salt.

The cathode 14 is preferably formed of a depolarizable and reversible material, examples of which include various conducting polymers, disulfide polymers and ion insertion materials. Examples include, but are not limited to 1) metal/metal hydride combinations ($M + 2H^+ \rightarrow MH_2$)
2) materials which undergo a cation insertion procedure such as Prussian Blue or materials into which metallic ions can be intercalated $$M^+ + ne^- + WO_3 \rightarrow M_nWO_3$$

$$K^+ + KFe(Fe(CN)_6 \rightarrow K_2Fe(Fe(CN)_6$$

$Li^+$ insertion is not preferred because of its hygroscopic nature; $K^+$ is a more suitable alternative.

3) Conducting polymers such as composites of polyaniline and 2,5 dimercapto-1,3,4 thiadiazole or Emeraldine iodide.

The anode 20 is preferably a stable, porous metal, electrically conducting oxide or a conductive composite which may be applied by standard coating or printing techniques on a surface or a fabric which incorporates the electrodes and electrolyte. The term "stable" means that the anode is not detrimentally modified by the oxidant that is generated. The anode material must also be electrocatalytic to halide oxidation. Materials used as fuel cell anode materials are suitable in this application. The anode can be either or both a photo-anode and an electro-anode. A suitable example is Pd coated, dye sensitive $TiO_2$. A preferred technique of applying the anode material to the fuel cell assembly is screen printing.

The porous surface layer 22 comprises a permeable film or membrane which serves to transport the electrochemically generated oxidant to the surface where it reacts with the chemical or biological agent to decontaminate the surface of the assembled structure. The membrane material is preferably hydrophobic but at the same time allows water as a liquid or vapor to permeate into the membrane to combine with the oxidant, (for example, $H_2O+I_2 \rightarrow HOI+HI$) while protecting the anode surface below. The membrane may also include a porous hydrophobic or superhydrophobic outer surface 28 of the same or a different material. Preferred characteristics of the surface 28 are that it allows transport of moisture from the environment there through so the moisture can react with the oxidant, and the oxidant in its generated form before and after reaction with the moisture can be transported through the surface to react with the contaminant. The surface should be chemically stable so that it does not react with the oxidant or the external contaminant. It should also be washable with common cleaning solutions and resistant to water (hydrophobic or superhydrophobic) while at the same time preventing penetration by those liquids to allow damage of the lower layers. As an added feature, the surface may include a chemical, bio- or photocatalyst to aid in the decomposition of contaminants that contact the surface.

The electrochemical cell 12 is connected to a switched (i.e., on-off) power source 24 which, when switched on, creates an electron flow through the electrochemical cell 12. Alternatively the anode 20 can be photo-activated (i.e., a photocell), causing electrons to flow when exposed to light. The coated device, structure or substrate 10 can also include one or more sensors 26 capable of detecting chemical or biological agents, which, upon exposure to that agent will activate a shunt and/or the power source 24 causing current to flow through the multi-layered electrochemical cell 12 structure, thus producing or releasing the oxidant at the anode, which, in turn, will chemically oxidize the agent, deactivating or decomposing the agent. Alternatively, solar radiation incident on the light-activated anode 20 will generate electron flow photochemically releasing the oxidants. The decomposition/generation rate of the oxidant is dependent on the level (amount) of current applied and the direction of current flow, i.e., the greater the current applied the greater the flow of oxidant generated.

Figure 2A:
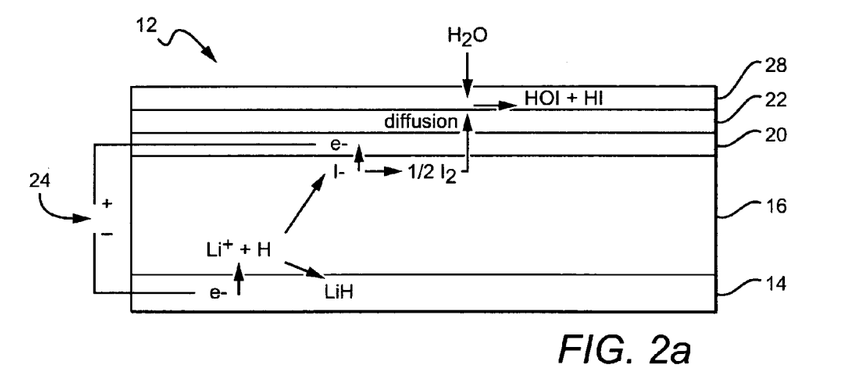
FIGS. 2a and 2b are schematic drawings of the assembly of FIG. 1 illustrating the operation of two embodiments of an electrochemical cell for decontamination of an assembly following exposure to a contaminant.
Figure 2B:
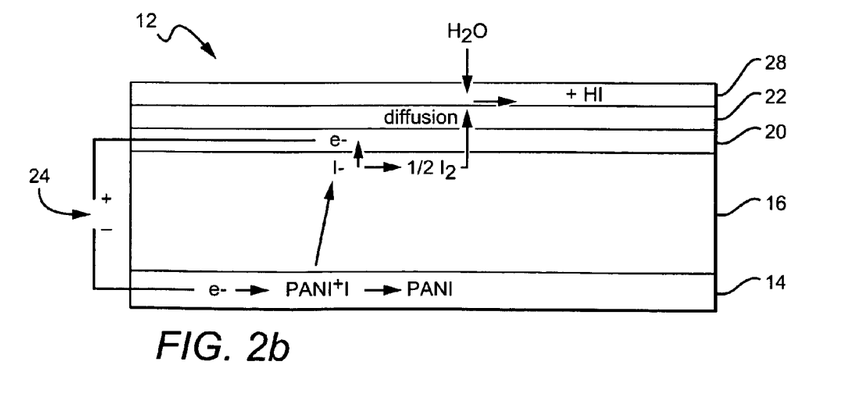

FIGS. 2a and 2b are schematic drawings illustrating the chemical reactions in two embodiments of the electrochemical cell 12. FIG. 2a utilizes a LiI/HI system; FIG. 2b uses a PANI source. Once activated, electrons flowing from the power source 24 (or the photocell/anode 20) connected to the electrochemical cell 12 causes oxidation of the iodide in the electrolyte layer 16 and/or cathode 14 to elemental iodine ($I_2$) which permeates through to the porous hydrophobic surface 22 where it combines with moisture from the environment and disproportionates according to the formula:

$I_2 + 2H_2O \rightarrow H^+ + I^- + HOI$

A typical power source provides 5V at 1-10 μamp/cm², preferably about 0.01 amp/cm². The HOI (I has a +1 valence) then reacts with the contaminating agent in contact with the surface layer 22, 28 of the electrochemical cell 12 on the substrate 10. It has been found that a loading of about $3\%_w$ of iodine, provided as a iodide, per cm² of coated surface will provide a continuous flow of a decontaminating agent to the cell surface 28 for about two hours of continuous activation. A typical loading is from about 1 mg/cm² to at least about 10 mg/cm².

An experimental cell constructed as in FIG. 2b with PANI iodide cathode, an electrolyte containing EC, PC, PAN, TPAI (34:50:7.77:7.77 by weight), a Teflon fabric separator and a platinized carbon anode was polarized with a positive voltage applied to the anode vs the cathode for five minute intervals.

Iodine flowing from the coating was detected by exposure to a disk of Watman #44 filter paper which was previously soaked in 0.5 M KI and then dried. A 6 mm diameter disk cut from the paper was placed over the multilayer coating to react with the evolving elemental iodine. The reaction immobilized the evolved $I_2$ vapor as brown $KI_3$ product within the paper through the reaction:

$\frac{1}{2}I_2(gas) + KI(solid) \rightarrow KI_3(solid)$

Subsequently, the exposed disk containing immobilized elemental iodine develops an intense blue complex when placed in a test tube to which is added 2 mL of 1% starch solution (Aldrich 319554). Iodide, $I^-$, develops no color. The blue color developed by the reaction of the starch indicator with the filter-paper disks exposed for 10 minute periods darkens as bias increases, evidencing an increase iodine output. Using this method, the blue indicator was observed for nine sequential 10 minute exposures at 3 V. The iodine continues to evolve for 90 minutes of accumulated activation.

A first example uses a cathode 14 comprising a combination of Ketjen black (an oil furnace carbon black) and PANI iodide, preferably $21\%_w$ Ketjen black and $79\%_w$ PANI iodide, and an electrolyte layer 16 comprising a polyacrylonitrile (PAN) gel 17, from about 7 to about $8\%_w$ tetrapropyl ammonium iodide (TPAI) 18, from about 33 to about $34\%_w$ ethylene carbonate (EC), from about 48 to about $50\%_w$ of propylene carbonate (PC) and from about 8 to about $12\%_w$ of PAN.

The anode 20 comprised platinized carbon with a PVA (Polyvinyl alcohol) binder, platinized woven carbon fabric, or a platinized carbon fiber tissue (obtained from Tech Fiber Products), preferably about $1\%_w$ Pt in carbon. The surface covering/membrane 22, 28 was a hydrophobic porous membrane or microporous filter paper, typically coated with a polyurethane or a fluorocarbon formed of Teflon®, Fluorothane™ or Sartech H. As an alternative a Teflon separator may also be placed between the electrolyte and the anode and Ag or activated $TiO_2$ may be added to the surface coating/membrane.

A second example of the layered electrochemical cell 12 comprises:
1) a cathode 14 comprising a coating formed from a paste of ground 2,5 dimercapto-1,3,4 thiadiazole, a conducting polymer, such as set forth in U.S. Pat. No. 5,665,492, dispersed in a carrier liquid, forming a flowable liquid that is painted on the device, structure or substrate. Alternatively, polyanaline iodide (PANI iodide) is electrodeposited or otherwise deposited on the surface. As a third alternative, Prussian Blue is electrodeposited on the substrate or it can be dispersed in a carrier liquid and painted on the surface.

2) The electrolyte layer 16 comprises a hydrophobic ionic layer which includes a halide containing compound 18, for example KI or other solid or gel electrolyte containing KI.

3) The anode 20 is a porous, solid conductor which can be formed from a slurry or dispersion of carbon black, platinized carbon black or Pd metallized $TiO_2$. The anode 20 may also include a photosensitizer such as Ru(II)bipyridyl (N719, Solaronix, SA).

4) A porous hydrophobic or superhydrophobic surface layer 22 is then provided by a fluorocarbon polymer.

Examples illustrating preparation of several of the components are as follows:

PANI Iodide. PANI iodide was prepared by forming a slurry of 3 gm. of the oxidized form of PANI (emeraldine base) in an excess of 1 M HI in deionized water an mixing for 16 hours with stirring. The mixture was filtered and the PANI iodide residue was recovered and washed with cold deionized water.

Electrolyte. A mixture 33.33 parts ethylene carbonate (CAS 96-49-1), 48.39 parts proplylene carbonate (CAS108-32-7), 7.53 parts tetrapropylammonium iodide (CAS 631-40-3) and between 7.53 and 10.75 parts polyacrylonitrile (CAS 25014-41-9) was heated in a water bath at 85-90° C. to form a solution suitable for casting or spreading on the solid substrate to form a thin film. Alternatively the solution was used to saturate a cloth formed of a dielectric material. The resulting liquid formed a gel within three days and was completely gelled within a week. The electrolyte film can be formed on a surface or within a porous fabric, such as an open weave Teflon separator. However, this application technique is merely representative and any approach that results in an ionically conducting solid or gelled electrolyte film containing the precursor to the oxidant (iodide in this example) can be used.

Cathode. 0.265 gm of Ketjen black (carbon), 0.9937 gm of PANI iodide (prepared as above) were mixed with 12.256 gm of N-methyl pyrrolidone (NMP) with sonication. The resulting mixture formed an ink that was painted on the substrate and heated to 80-100° C. for 1 hour to dry and cure. When the cathode was applied to a non-conducting surface provision is made to contact the cathode with a copper foil adhesive tape (3M Cu conductive tape) lead. The lead was over-coated with a uv cured epoxy to assure good contact.

Anode. Anodes were prepared by dipping a conducting carbon fabric in a chloro-platinic acid solution for 5 minutes. The wetted fabric was dried at 90° C. and then heated in a furnace at 300° C. for 5 minutes. The anode can then be coated with a thin hydrophobic lacquer such as Sartech H or Fluorothane™. However, other hydrophobic coatings can also be used.

Coating Assembly. On any substrate the cathode is applied using common coating techniques, a conductive lead is attached and then a layer of electrolyte is applied. The electrolyte may be contained in a highly porous dielectric fabric separator. While the electrolyte is still a liquid, the anode is placed on the surface and a copper tape lead is also attached to the anode.

Hydrophobic Top Coating. After the cell is completely assembled, a porous hydrophobic coating or film is applied such as by overlaying a microporous filter paper film or coating with Sartech H or Fluorothane™. Other thin, porous hydrophobic coatings can be considered, but a superhydrophobic and biocidally active coating that passes elemental iodine is preferred. A superhydrophobic surface can be obtained by providing a roughed hydrophobic surface or coating a roughened surface with a hydrophobic material which increases the contact angle between a water droplet and the non-wettable surface on which it rests. Alternatively, the top coat can be applied to the anode during the anode assembly, as described above.

Cell Capacity. The typical weight of the active component of the electrolyte is 0.01 gm $TPAI/cm^2$ of film. This is equivalent to (0.01 gm/313.27 gm/mol) mol. TPAI or a theoretical capacity of (0.01 gm/616.54 gm/mol ~16 µmol) $I_2$. Experiment results show that $e\ coli$ 0157H7 can be killed in 300 sec or less at an average current density of 0.001 $A/cm2$. From Faraday's Law, this quantity of charge corresponds to 0.3 coul. or 1.6 µmol of $I_2$, assuming a 100% current efficiency for the $I_2$ production. Hence, the cell can provide 10 cycles of kills using such an assumption of efficiency. It is unlikely that the efficiency for $I_2$ production is 100%. Therefore the observed kill likely used substantially less $I_2$ than that indicated by the total charge passed. The 10 cycles estimate represents a lower limit for the number of kills for this microbe. It is likely that the number of practical cycles is considerably greater since the true current efficiency of the cell remains low. Furthermore, the capacity of the cell will can be increased by using a thicker electrolyte film having optimized or greater iodide loading. Data indicates that several µcoul will generate sufficient quantities of $I_2$ as evidenced by complete staining of a piece of filter paper with KI/starch indicator.

In each instance following activation and depletion of the oxidizer content in the electrochemical cell, the electrochemical cell can be reactivated by applying an iodide salt such as a tetra-propylammonium iodide solution to the surface 28 and, if necessary, applying a reverse polarization.

Figure 3:
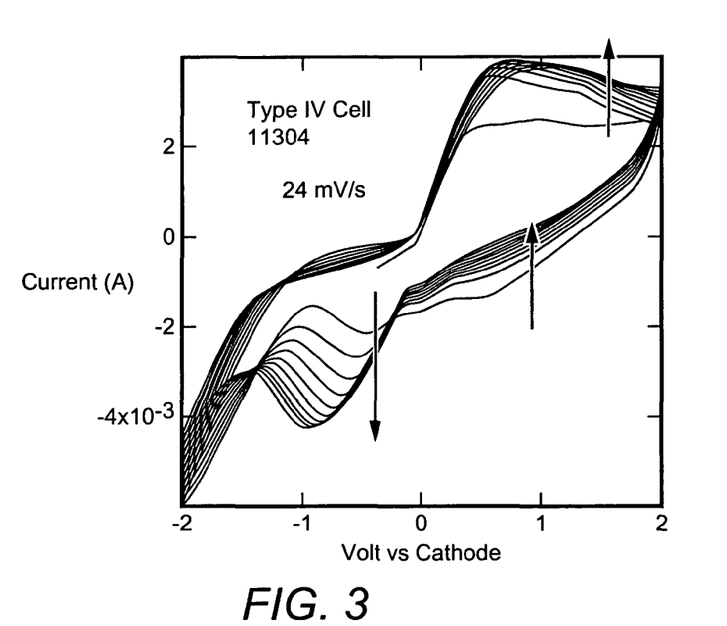
FIG. 3 is a graph showing the recycle curve for an electrochemical cell as shown in FIG. 1.
Figure 4:
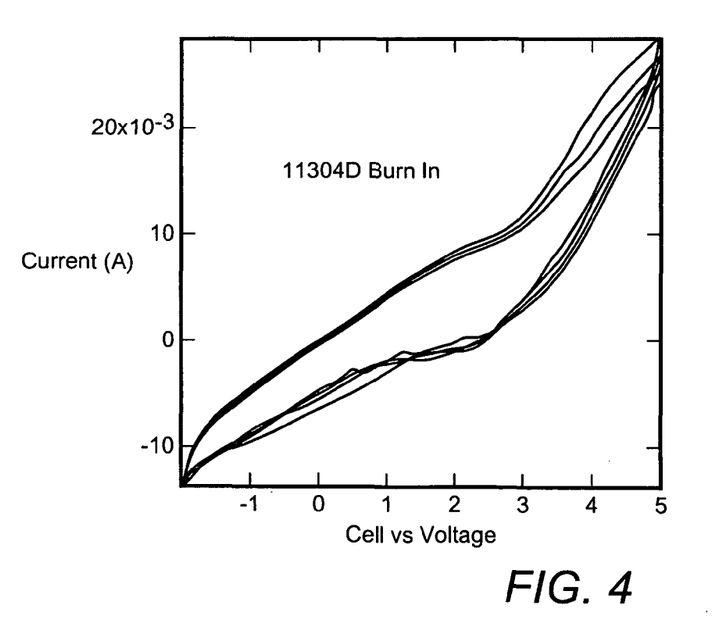
FIG. 4 is a graph showing the recycle curve for a different cell of the same construction.
Figure 5:
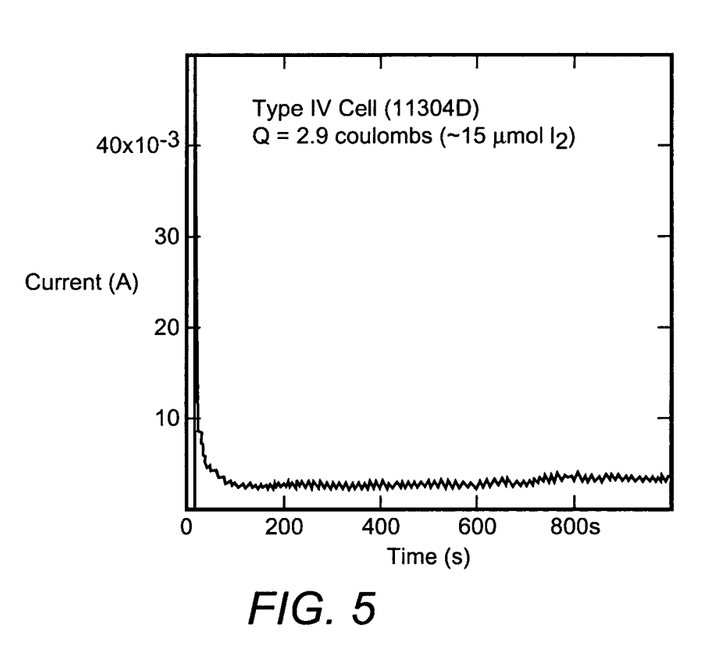
FIG. 5 is a graph showing the current flow for continuous operation of an electrochemical cell.

FIG. 3 is a graph showing the recycle curve for an electrochemical cell comprising the carbon black/PANI cathode, the TPAI/PAN electrolyte, a platinized carbon fiber anode and a Sartech H membrane as described above operated at 5V. Delivery of iodine to the surface occurs with positive current flow and ceases when the current flow is reversed. FIG. 4 is a graph showing the recycle curve for the burn in of a different cell of the same construction FIG. 5 is a graph showing the current flow for continuous operation of an electrochemical cell, the cell having the same construction as that used to generate the graph of FIG. 3, containing about 15 µmols of $I_2$. While this graph only illustrates operation for 1000 seconds (approximately 17 minutes), there is a continuous flow of $I_2$ for at least 1 hour.

Figure 6:
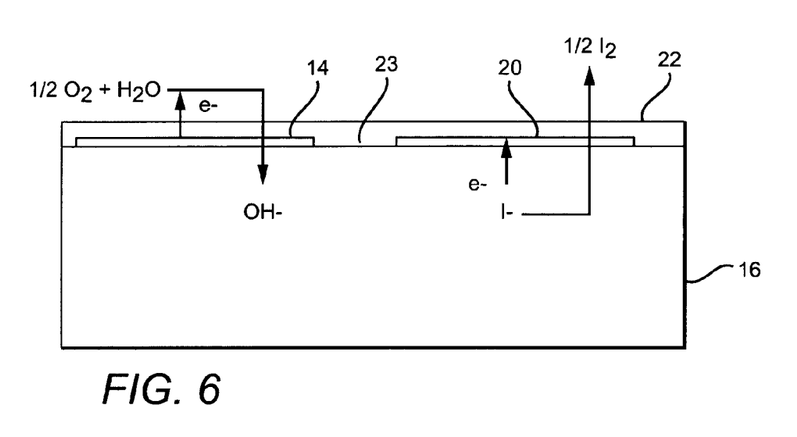
FIG. 6 is a schematic drawing of a device having coplander electrodes.

FIG. 6 shows an alternative embodiment which includes an electrolyte 16 with the anode 20 and cathode 14 both being located on the same surface of the electrolyte layer 16 but spaced apart to form a space or gap 23 therebetween with the porous surface layer 22 covering the anode 20 and cathode 14 and filling the space or gap 23 between them. A typical gap 23 is from about 0.001 mm to about 0.5 mm, preferably, from about 0.05 to about 0.25 mm. In a preferred embodiment of this construction the cathode 14 is an air cathode. In a further variation the anode 20 and cathode 14 can be inter-digitated, but still spaced apart as shown in the top view of FIG. 7. Moisture and oxygen from the surrounding atmosphere passes through the porous surface layer 22 to cathode 14, causing electrons to flow through the electrolyte layer 16 and the oxidant to be released from the anode 20, cathode 14 or electrolyte 16 which contains the oxidant precursor. The anode 20 can comprise materials as discussed hereinabove. Suitable materials for construction of an air cathode are those typically used in fuel cells. Examples include, but are not limited to platinum, platinized carbon, platinized titanium, conducting oxides and conducting polymers such as PANI.

Figure 8:
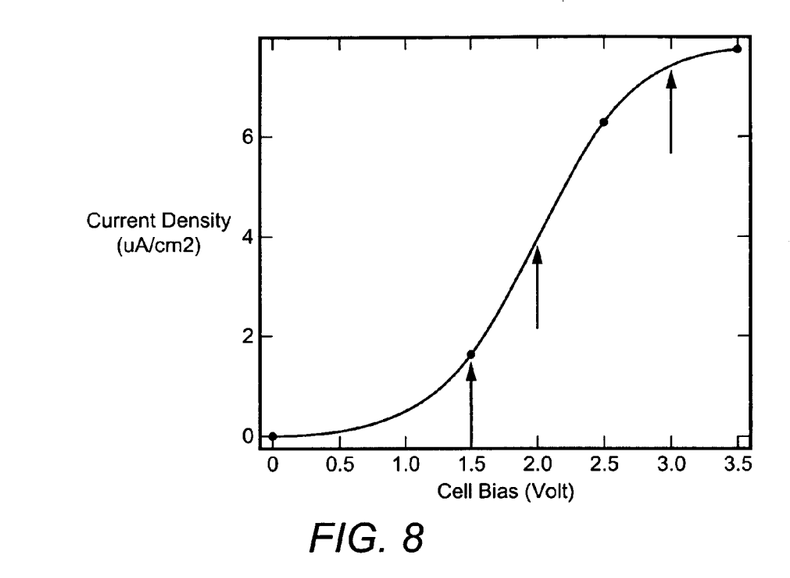
FIG. 8 is a graph of cell bias vs. current density for a typical device incorporating features of the invention.

FIG. 8 is a graph of applied voltage (cell bias) vs. current density for a typical cell incorporating features of the invention. To demonstrate evolution of iodine from the surface of the cell suitable iodine collectors, such as a sheet of filter paper as described above, were placed on the device surface, and exposed to gases generated at the surface at various applied voltages (as indicated by the arrows on FIG. 8) to collect evolving gases for a predetermined period of time, the quantity of iodine produced being indicated by reaction with a starch solution. If iodine is present a reaction occurs between the iodine and the starch and a colored stain appears on the paper, the quantity of iodine being qualitatively shown by the amount of color (darkness) of the stain produced. The cell used to generate the curve of FIG. 8 appears to have a threshold potential of about 2 volts. Below about 2 volts no iodine appears to evolve. At 3 volts a significant quantity of iodine is continuously generated, as evidenced by a dark stain. At voltages between 2 and 3 increasing amounts of iodine continuously evolve as evidenced by a gradient of staining, from very light to dark obtained at about 3 volts or greater.

The threshold appears to depend on cell geometry, electrolyte conductivity and cell iodine concentration. Iodine evolution appears to be time dependent with the total evolved iodine being primarily dependent on the quantity in the cell and the amount evolving on a per time basis (i.e., per minute) depending primarily on the cell bias in excess of the threshold voltage, applied to the cell. The lower the applied voltage the slower the iodine will evolve.

Figure 7:
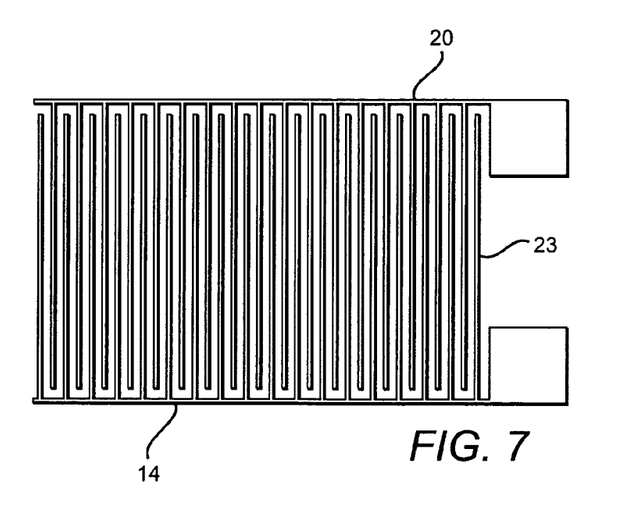
FIG. 7 is a top view of a device as shown in FIG. 6 where the electrodes are interdigitated.
Figure 9:
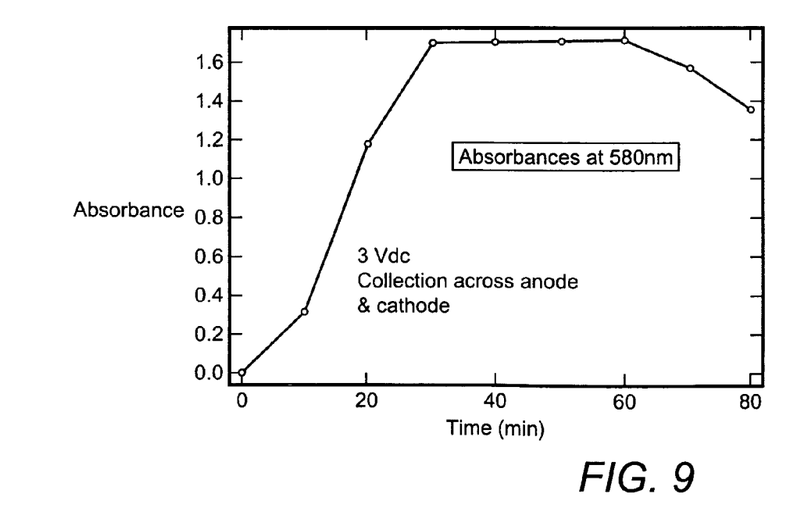
FIG. 9 is a graph showing the time dependent evolution of iodine for a typical cell in accordance with FIGS. 6 and 7 at 3 volt bias.

FIG. 9 is a graph showing the evolution of iodine from the surface of an interdigitated cell as shown in FIGS. 6 and 7 over a period of 80 minutes, the amount of iodine evolving over the 80 minute period being indicated by UV-VIS absorption at 580 nm measured for the starch/iodine complex at selected intervals in that time period. There appears to be a time delay of about 20 minutes until a relatively stable iodine evolution is obtained, but thereafter, until the iodine in the cell is dissipated, there appears to be a relatively stable evolution of iodine for about one hour at a cell bias of about 3V.

A first preferred embodiment of the self-decontaminating surface described herein comprises applying a carbon-PANI-iodine coating to a metal substrate followed by the electrolyte and the porous anode. An alternative construction utilizes a flexible cloth or blanket of material comprising a porous carbon felt soaked with PANI-iodide to form the cathode followed by a layer of the electrolyte and then a porous carbon felt anode. Furthermore, a structure comprising a porous felt anode, an electrolyte, a PANI-iodide soaked felt cathode, an electrolyte, and a porous felt anode can be fabricated with leads on the respective anodes and cathode. The cloth can then be rolled up or pleated to provide a high surface area structure which can serve as an active filter and generate decontaminating agent for an enclosed environment.

Figure 10:
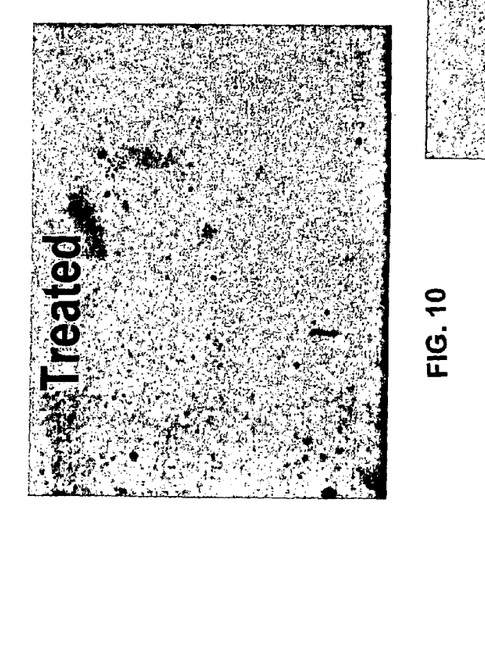
FIG. 10 is a photo micrograph showing an *e coli* contaminated surface after exposure to iodine produced by an assembly as in FIG. 1.
Figure 11:
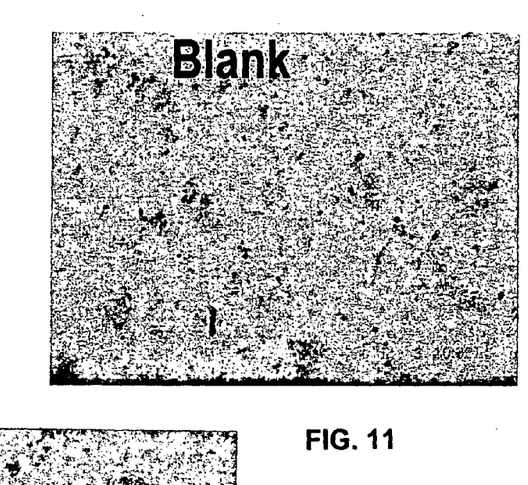
FIG. 11 is a photo micrograph of an *e coli* contaminated surface without treatment as set forth herein.
Figure 12:
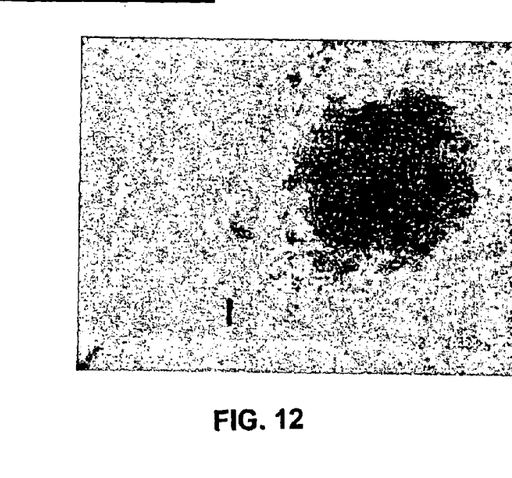
FIG. 12 is a photo micrograph of dead *bacillus subtillis* cells on a surface following treatment as set forth herein.

FIGS. 10-12 illustrate the effectiveness of devices incorporating features of the invention in destroying biological contaminants deposited on the surface of the cell. FIG. 10 shows a surface incorporating features of the invention following contamination with *e coli*, treatment for 1 hour at 5V and 2.9 coulombs releasing approximately 15 μmol $I_2$ and then incubation. FIG. 11 shows a similar contaminated surface without release of $I_2$. FIG. 12 shows dead cells on a surface incorporating features of the invention contaminated with *bacillus subtillis* and decontaminated for a period of 1 hour as described herein.

While the incorporation of halogen salts or compounds which can electrochemically release halogen oxidants is described herein, the invention contemplated is not so limited. One skilled in the art will recognize that other compounds can be used in the same structural arrangement to electrochemically release a decontaminating oxidant on demand. These include, but are not limited to, peroxides, ammonia, permanganates and other known electrochemically generated oxidizing agent.

We claim:

1. An electrically activated, self-decontaminating multi-layered electrochemical cell comprising an adherent film for application to a surface of a device, structure, substrate, or an enclosed space, said electrochemical cell including an electrolyte layer, at least one of a cathode film and an anode film on upper or lower surfaces of said electrolyte layer, the electrolyte layer comprising a precursor for an oxidizing chemical, said precursor electrochemically releasing said oxidizing chemical, said oxidizing chemical effective for decontaminating said surfaces exposed to a contaminating biological or chemical agent, wherein the cathode film is a coating on the surface of the device, structure, substrate or enclosed space, the electrolyte layer is a coating on said cathode film, the anode film is a coating on the electrolyte layer and a hydrophobic porous surface layer is on the anode film, the precursor for said oxidizing chemical being located within the electrolyte layer, the cathode film or both the electrolyte layer and the cathode film.

2. The structure of claim 1 wherein the electrolyte layer comprises a matrix of
   a) a nonconductive, hydrophobic, solid electrolyte selected from the group consisting of polyethylene oxide, a perfluorinated polymer and crystalline $RbAg_4I_5$, or
   b) ionic semi-liquid gels selected from the group consisting of quaternary alkyl ammonium in alkyl carbonate/polyacrylonitrile (PAN) gels and solgels derived from porous silica gels formed from tetraethyl orthosilicate and polyethylene glycol, which are each doped with an ionic liquid containing a halide releasing compound.

3. The structure of claim 1 wherein the cathode film is a depolarizable and reversible material selected from the group consisting of conducting polymers, disulfide polymers, ion insertion materials, a coating formed from a paste of ground 2,5 dimercapto-1,3,4 thiadiazole, polyanaline (PANI) iodide, and Prussian blue.

4. The structure of claim 1 wherein the cathode film comprises a combination of carbon black and polyanaline (PANI) iodide.

5. The structure of claim 1 wherein the anode film is porous metal, electrically conducting oxide or a conductive composite.

6. The structure of claim 1 wherein the anode film comprises platinized carbon with a polyimide binder, platinized woven carbon fabric, or a platinized carbon fiber tissue.

7. The structure of claim 1 wherein the porous surface layer comprises a hydrophobic porous membrane or microporous filter paper.

8. The structure of claim 1 wherein the porous surface layer comprises a polyurethane-coated or a fluorocarbon-coated membrane.

9. The structure of claim 8 wherein the porous surface layer further includes Ag or activated $TiO_2$.

10. The structure of claim 1 further including a source of electrons to electrochemically release the oxidizing chemical.

11. The structure of claim 10 wherein the source of electrons is a battery or a photocell.

12. The structure of claim 1 further including a sensor for the contaminating biochemical or chemical agent, said sensor upon detecting the presence of the agent activating the multilayered electrochemical cell causing release of the oxidizing chemical.

13. The structure of claim 1 wherein the electrochemical cell is formed into a rolled or pleated structure, providing a high surface area.

14. The structure of claim 1, wherein the multilayered electrochemical cell is an applique arranged to adhere to said surface of a device, structure, substrate, or enclosed space.

15. A surface comprising at least one multilayered electrochemical cell according to claim 1.

16. An enclosed space comprising at least one multilayered electrochemical cell according to claim 1.

17. The structure of claim 1, wherein said adherent film is applied to said surface of a device, structure, substrate, or an enclosed space by brushing, roiling, spraying, or pouring.

18. The structure of claim 17, wherein said adherent film includes a carrier.

19. The structure of claim 18, wherein said carrier is a water- or organic solvent-based carrier or a polymeric material.

20. An electrically activated, self-decontaminating multilayered electrochemical cell comprising an adherent film for application to a surface of a device, structure, substrate, or an enclosed space, said electrochemical cell including an electrolyte layer, at least one of a cathode film and an anode film on upper or lower surfaces of said electrolyte layer, the electrolyte layer comprising a precursor for an oxidizing chemical, said precursor electrochemically releasing said oxidizing chemical, said oxidizing chemical effective for decontaminating said surfaces exposed to a contaminating biological or chemical agent, wherein the electrochemical cell comprises a cathode film and an anode film positioned in a coplanar manner on the electrolyte layer with a gap there between and a hydrophobic porous surface layer covering the anode film and cathode film and filling the gap there between, the precursor for said oxidizing chemical being located within one or more of the electrolyte layer, the cathode film or the anode film.

21. The structure of claim 20 wherein the gap between the anode film and cathode film is from about 0.001 mm to about 0.5 mm in width.

\* \* \* \* \*